United States Patent [19]

Beech, Jr. et al.

[11] Patent Number: 4,973,790
[45] Date of Patent: Nov. 27, 1990

[54] PROCESS FOR UPGRADING LIGHT OLEFINIC STREAMS

[75] Inventors: James H. Beech, Jr., Wilmington, Del.; Francis P. Ragonese, Cherry Hill; James A. Stoos, Blackwood, both of N.J.; Sergei Yurchak, Media, Pa.

[73] Assignee: Mobil Oil Corporation, New York, N.Y.

[21] Appl. No.: 437,138

[22] Filed: Nov. 16, 1989

[51] Int. Cl.$^5$ .............................. C07C 2/02; C07C 2/04
[52] U.S. Cl. .................................. 585/533; 585/330; 585/518; 208/70
[58] Field of Search ................. 585/533, 330, 518; 208/70

[56] References Cited

U.S. PATENT DOCUMENTS

| 2,558,137 | 6/1951 | Hepp | 583/518 |
|---|---|---|---|
| 2,775,637 | 12/1956 | Lanning et al. | 585/518 |
| 3,432,573 | 3/1969 | Keil | 585/518 |
| 3,960,978 | 6/1976 | Coiven et al. | 585/533 |
| 4,070,411 | 1/1978 | Butter et al. | 585/533 |
| 4,417,087 | 11/1983 | Miller | 585/533 |
| 4,513,156 | 4/1985 | Tabak | 585/517 |
| 4,542,251 | 9/1985 | Miller | 585/533 |
| 4,544,792 | 10/1985 | Smith et al. | 585/533 |
| 4,554,396 | 11/1985 | Chang et al. | 585/533 |
| 4,675,460 | 6/1987 | Seddon et al. | 585/533 |
| 4,754,096 | 6/1988 | Chang et al. | 585/533 |
| 4,777,316 | 10/1988 | Harandi et al. | 585/517 |
| 4,855,524 | 8/1989 | Harandi et al. | 585/533 |
| 4,865,718 | 9/1989 | Herbst et al. | 585/530 |

Primary Examiner—Helane E. Myers
Attorney, Agent, or Firm—Alexander J. McKillop; Charles J. Speciale; Richard D. Stone

[57] ABSTRACT

A process for oligomerizing C2 to C10 olefins obtained by catalytic cracking of heavy crude oil is disclosed. The olefins are oligomerized in the presence of added hydrogen over a shape selective zeolite to gasoline and distillate products. Feed pretreatment, to remove basic nitrogen compounds present in light olefin stream in refinery, with water wash or a guard bed is practiced improves catalyst life.

15 Claims, 3 Drawing Sheets

FIG. 3

PROCESS FOR UPGRADING LIGHT OLEFINIC STREAMS

BACKGROUND OF THE INVENTION

1. Field of the Invention

The invention relates to upgrading of light olefinic streams, ranging from ethylene containing streams up to naphtha boiling range materials, to produce high quality distillate and motor fuel.

Upgrading of light olefinic streams by oligomerization over acid-type catalysts has long been known. Solid phosphoric acid catalysts, or liquid phosphoric acid on a support, were used to polymerize propylene and butenes to gasoline boiling range materials. The acid required a certain amount of water, so contacting the feed with water was a convenient way to add water, and also to remove nitrogen compounds which were catalyst poisons. The nitrogen content of the feed had to be limited to less than 50 ppm basic nitrogen for satisfactory life of the phosphoric acid catalyst.

An extensive review of more modern oligomerization technology, and much experimental work, was reported by W. E. Garwood, in Conversion of C2–C10 to Higher Olefins over Synthetic Zeolite ZSM-5, ACS Symposium Series, No. 218, Intrazeolite Chemistry, Galen D. Stucky and Francis G. Dwyer, Editors, Copyright 1983 by the American Chemical Society.

Garwood reported that ethylene was far more difficult to convert than higher molecular weight olefins. At 400 psig, in a temperature range of 400–600° F., at some temperatures 95% conversion of propylene in feed was achieved while only 5% conversion of ethylene in feed occurred.

Garwood used commercial grade olefin feed stocks, of greater than 95% purity. The effect of nitrogen contaminants was not discussed. The effect of hydrogen on yields and catalyst life was not investigated. Some experiments were conducted in the presence of hydrogen, but the hydrogen was used, with nitrogen, as a diluent so that the catalyst would see an olefin partial pressure of 1–2 psia while the total pressure was 1 atmosphere.

The patent literature also reports much work on converting lower olefins to gasoline and distillate.

U.S. Pat. No. 4,544,792, which is incorporated herein by reference, contains an extensive review of olefin oligomerization developments. This reference reported that moderate temperature and relatively high pressure could be used to favor aliphatic, distillate range product. Lower olefinic feedstocks containing C2–C8 alkenes could be converted, however, these conditions which favored production of relatively high boiling distillate do not convert a major fraction of ethylene.

In the upgrading of Fischer-Tropsch olefins, it has been found beneficial to water wash a C3–C7 olefinic stream to reduce the oxygenate content to below 1 Wt %, followed by oligomerization in a pressurized reactor in the presence of hydrogen. U.S. Pat. No. 4,544,792 reported that feedstocks containing trace amounts of oxygenates could be catalytically upgraded over H-ZSM-5 when as little as 1 mole % H2 was present. When increased oxygenate concentrations were encountered, more hydrogen was required. The cofed hydrogen inhibited the formation of coke on the catalyst.

A related approach to the problem of dealing with oxygenates in Fischer-Tropsch liquids is disclosed in U.S. Pat. No. 4,513,156, which is incorporated herein by reference. A more aggressive extraction of oxygenates was practiced, to remove essentially all of the oxygenates upstream of the olefin oligomerization reactor. A multi-stage vertical extraction columns was used for water washing or extracting oxygenates from the feed.

Upgrading of pyrolysis naphtha produced during steam cracking to make ethylene, by passing the naphtha over Pd/Zn/ZSM-5 at 900° to 1200° F. was disclosed in U.S. Pat. No. 4,097,367, which is incorporated by reference. The high temperature processing of the pyrolysis naphtha converted to aromatics everything boiling in the BTX range, yielding a liquid product with essentially no non-aromatic hydrocarbons boiling above 167° F. The patentee discussed the general prejudice in these arts re. the presence of hydrogen, namely that ZSM-5 is known for conversion of olefins to aromatics, but preferably in the absence of hydrogen.

Refiners have been reluctant to subject olefinic streams to hydrotreating, or to catalytic hydroprocessing, out of concern that the olefins would be saturated. In gasoline boiling range materials this saturation would greatly decrease the gasoline octane. In C2 to C4 olefins, saturation of the olefins would reduce greatly their reactivity, and reduce the value of these materials. C2 olefins are very difficult to oligomerize, and C2 paraffins are even less reactive. The presence of large amounts of basic nitrogen in these streams makes hydrotreating desirable, but the need to preserve olefins makes it unwise.

We reviewed the work that others had done, for guidance on how best to upgrade refinery olefin containing streams to heavier, more valuable products. Two types of problems are present, feed contamination and presence of materials which are not contaminants but a difficult to process.

Feed contamination is a severe problem with olefinic streams in a refinery because these streams usually contain large amounts of sulfur and nitrogen. Much of the nitrogen contamination is introduced in trying to reduce the sulfur contamination, i.e. amine scrubbing removes sulfur but leaves trace amounts of amine in the scrubbed stream.

The presence of basic nitrogen in the light olefins refinery streams can damage the zeolite oligomerization catalysts, so it would be beneficial if a way could be found to make these catalysts more tolerant of catalyst poisons which are always found in refinery olefin streams. A better feed pretreatment process is needed, which can reduce the level of nitrogen contaminants in the feed at least two orders of magnitude below the 50 ppm tolerated by the phosphoric acid olefin oligomerization process. The feed pretreatment process should also be able to tolerate momentary overloads and upsets, while still protecting the zeolite catalyst.

The feed pretreatment process should be one which can operate continuously, or at least for long periods using a regenerable, rather than a replaceable, nitrogen removal medium. Feed pretreatment can be further complicated by the presence of large amounts of unusual contaminants in refinery light olefin streams, especially the presence of large amounts of dienes. Some of these contaminants, probably the dienes, can irreversibly deactivate some nitrogen removing materials. Thus a conventional nitrogen sorbent which is regenerable in some other service might not prove suitable for use in feed pretreatment of light olefinic streams prepared by high temperature thermal and/or catalytic processing of crude oil.

Another problem with light olefinic streams from a refinery, besides the difficulty in pretreating such streams, is that refinery propylene frequently contains large amounts of ethylene. It would be beneficial if an upgrading process were available which could efficiently convert ethylene as well as heavier olefins.

It is also important to have a catalytic olefin upgrading process which can operate for a long time, at relatively high severity and at relatively high space velocities.

We have discovered a feed pretreatment process which provides an ideal way to efficiently remove basic nitrogen contaminants from refinery light olefin streams and make these streams suitable for downstream zeolite upgrading.

We have also discovered an efficient light olefin upgrading process, which can tolerate, e.g., the presence of large amounts of ethylene in a propylene rich stream, and which will efficiently convert a mixture of light olefins to heavier, more valuable normally liquid products. The olefin upgrading process tolerates the presence of relatively large amounts of dienes.

BRIEF SUMMARY OF THE INVENTION

Accordingly, the present invention provides a process for upgrading a feed comprising C2 to C10 olefins containing basic nitrogen compounds which has been produced by thermal or catalytic cracking of a heavy hydrocarbon feed by contacting the feed with an upgrading catalyst comprising a zeolite having a Constraint Index of about 1 to 12, a silica to alumina mole ratio of at least 12 at olefin oligomerization reaction conditions including a superatmospheric pressure and in the presence of hydrogen at a hydrogen to hydrocarbon ratio of about 0.01:1 to 1:1 to oligomerize at least a portion of the olefins in the feed to gasoline and distillate boiling range products, and wherein the presence of hydrogen extends the catalyst life of the upgrading catalyst relative to operation at superatmospheric pressure without any hydrogen added.

In another embodiment, the present invention provides a process for oligomerizing a feed of a light, normally gaseous hydrocarbon stream containing more than 0.5 wt ppm basic nitrogen compounds and comprising olefinic hydrocarbons having three to four carbon atoms produced by catalytic cracking of heavy, sulfur containing hydrocarbons boiling in the gas oil and heavier range to lighter products and H2S, which lighter products are treated with an amine to reduce the H2S content and produce a light, normally gaseous hydrocarbon stream containing a reduced H2S content and more than 0.5 wt ppm basic nitrogen as a result of the amine treatment of the lighter products, to produce stable gasoline and distillate boiling range products comprising reducing the basic nitrogen content of the light, normally gaseous hydrocarbon feed by contacting said feed with a sorbent having an affinity for basic nitrogen compounds to reduce the basic nitrogen content of the feed below 0.1 wt ppm; and oligomerizing said feed with a basic nitrogen content below 0.1 wt ppm over an oligomerization catalyst comprising a zeolite having a Constraint Index of about 1 to 12 and a silica to alumina mole ratio of at least 12 at olefin oligomerization conditions to produce a gasoline and distillate boiling range product.

In a more limited embodiment, the present invention provides a process for producing gasoline and distillate boiling range products from a heavy hydrocarbon feed boiling in the gas oil and heavier range comprising catalytically cracking said heavy feed at catalytic cracking conditions in a catalytic cracking unit to produce cracked products including olefinic C3 and C4 hydrocarbons and H2S; treating the olefinic C3 and C4 hydrocarbons with an amine to reduce the H2S content thereof and produce treated olefinic C3 and C4 hydrocarbons containing more than 0.1 wt ppm basic nitrogen compounds as a result of the amine treating step; reducing the basic nitrogen content of the olefinic feed below 0.05 wt ppm basic nitrogen by extracting the basic nitrogen compounds from the feed with water to produce a water extracted olefinic feed with a reduced basic nitrogen content; and oligomerizing the water extracted olefinic feed by contact with an upgrading catalyst comprising ZSM-5 having a silica to alumina mole ratio of at least 12, and an alpha value, on a pure ZSM-5 basis, of at least 100, at olefin oligomerization conditions including a temperature of 350–750° F., the upgrading reaction is conducted in the presence of hydrogen, at a mole ratio of hydrogen to hydrocarbon of about 0.01:1 to about 0.5:1 and a hydrocarbon weight hourly space velocity of about 0.1 to 10 to oligomerize at least a portion of the olefins in the feed to a gasoline and distillate boiling range product.

DETAILED DESCRIPTION

Feedstocks

The feedstocks which are suitable for use in the present invention are any light olefinic fractions produced by thermal or catalytic cracking of crude oil fractions.

The preferred feedstocks are light olefin streams from a catalytic cracking unit. The process works especially well when the feed is an LPG fraction which has been treated with a basic nitrogen containing stream such as DEA, di ethanol amine, to remove sulfur compounds. The process tolerates very well C2 to C10 olefin containing streams containing in excess of 1 ppm basic nitrogen, though a feed pretreatment step will be necessary to reduce the basic nitrogen content.

An especially preferred feedstock in a liquified petroleum gas, LPG, containing 0.1 to 0.2 wt ppm basic nitrogen by conventional analytical methods, undetectable levels of sulfur, no more than 0.5 wt % dienes, less than 5 ppm ammonia, typically on the order of 2–4 ppm ammonia, no more than 1 ppm sodium and having a low content of other metals. Although such a feed might seem to be fairly clean for a commercially available LPG, it is difficult to treat using conventional olefin upgrading technology, and is therefore an ideal candidate for use in the practice of the present invention.

The process of the present invention can also be used for upgrading FCC naphtha, or coker naphtha or any naphtha obtained by a thermal or catalytic process.

Suitable naphtha feedstocks may be produced using the fluid-coking process described in U.S. Pat. Nos. 2,905,629; 2,905,733 and 2,813,916. The Flexicoking process may also be used. This process is identical to fluid-coking but converts coke to low BTU gas. Flexicoking is described in U.S. Pat. Nos. 3,661,543; 3,816,084; 4,055,484 and 4,497,705 which are incorporated herein by reference.

The naphtha boiling range streams may comprise C4–C12+ materials, and usually comprise C5–C12 materials. Expressed as a boiling range, the naphtha will usually have an initial boiling point of 60–150° F. or above, and an end boiling point in the range of 300–400° F. The process of the present invention tolerates even heavier charge stocks, those having an end point up to 450° or 500° F., but such materials are usually considered too heavy for use in a refinery gasoline pool and for that reason are not preferred feedstocks for use herein. They may be included in the feedstock to the process of the present invention, and the heavy ends removed from the product by distillation.

The unstable naphthas, such as coker naphtha, are not preferred feedstocks. The high diene content feeds polymerize at low temperatures and can cause a heat exchanger used to preheat the feed to plug. These materials tend to have ratios of n-olefins to paraffins in excess of 1. In the C6 to C12 range, these ratios frequently range from about 1.1 to 2.1. The ratio usually increases with increasing carbon numbers. Extensive analytical results of the composition of coker naphtha, and some of its characteristics, are reported in U.S. Pat. No. 4,711,968.

OLIGOMERIZATION CATALYST

The catalyst preferred for use herein comprises a shape selective zeolite having a silica to alumina ratio of at least 12 and a Constraint Index of about 1 to 12.

Any zeolite having a constraint index of 1–12 can be used herein as a shape selective zeolite additive. Details of the Constraint Index test procedures are provided in J. Catalysis 67, 218–222 (1981) and in U.S. Pat. No. 4,711,710 (Chen et al), both of which are incorporated herein by reference.

Preferred shape selective zeolites are exemplified by ZSM-5, ZSM-11, ZSM-12, ZSM-23, ZSM-35, ZSM-48, ZSM-57 and similar materials.

ZSM-5 is described in U.S. Pat. No. 3,702,886, U.S. Reissue No. 29,948 and in U.S. Pat. No. 4,061,724 (describing a high silica ZSM-5 as "silicalite").

ZSM-11 is described in U.S. Pat. No. 3,709,979.

ZSM-12 is described in U.S. Pat. No. 3,832,449.

ZSM-23 is described in U.S. Pat. No. 4,076,842.

ZSM-35 is described in U.S. Pat. No. 4,016,245.

ZSM-57 is described in U.S. Pat. No. 4,046,859.

These patents are incorporated herein by reference.

Zeolites in which some other framework element is present in partial or total substitution of aluminum can be advantageous. Elements which can be substituted for part of all of the framework aluminum are boron, gallium, zirconium, titanium and other trivalent metals which are heavier than aluminum. Specific examples of such catalysts include ZSM-5 or zeolite beta containing boron, gallium, zirconium and/or titanium. In lieu of, or in addition to, being incorporated into the zeolite framework, these and other catalytically active elements can also be deposited upon the zeolite by any suitable procedure, e.g., impregnation.

When shape selective zeolites are added, preferably relatively high silica shape selective zeolites are used, i.e., with a silica/alumina ratio above 20/1, and more preferably with a ratio of 70/1, 100/1, 500/1 or even higher.

Preferably the zeolites have relatively high acid cracking activity, or alpha activity. Preferably the alpha value of the pure zeolite is in excess of 100, and most preferably is about 150 to 250.

The high acid activity allows the desired conversion reactions to be achieved at relatively low temperatures, discussed hereafter. Somewhat higher temperatures can be tolerated, but this will increase the rate of gum formation and increase catalyst deactivation rates.

The Alpha test indicates the catalytic cracking activity of a catalyst compared to a standard catalyst. The Alpha test measures the relative rate constant (rate of normal hexane conversion per volume of catalyst per unit time). Highly active silica-alumina cracking catalyst has an Alpha of 1 (Rate Constant=0.016 sec $-1$). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), which are incorporated herein by reference. The Alpha test used herein ran at a constant 538 C with a variable flow rate, as described in the *Journal of Catalysis*, Vol. 61, p. 395.

PROCESS CONDITIONS

In general terms, the process of the present invention can be conducted within any of the process conditions heretofore found suitable for the conversion of olefins to gasoline and/or distillate components. More details of suitable process conditions may be taken from U.S. Pat. Nos. 4,150,062; 4,211,640 and 4,227,992 (Garwood et al) which are incorporated herein by reference.

It is preferred to keep temperatures fairly low to save energy. Low temperatures are preferred when there are large amounts of dienes in the feed.

The temperature, space velocity and catalyst alpha activity can all vary widely.

Acceptable, preferred, and most preferred reaction conditions are listed in the following table.

TABLE 1

| | Acceptable | Preferred | Most Preferred |
|---|---|---|---|
| Process Conditions | | | |
| Reactor Temp. | 200–900 | 250–750 | 300–550 |
| Pressure, psig | any | 100–1000 | 300–800 |
| WHSV (on olefin) | 0.1–100 | 0.2–20 | 0.5–5 |
| Delta T, F | 150 | 100 | 50 |
| Inert Diluent, mole % | 0–95 | 0–90 | 20–60 |

When a fluidized bed reactor is used the delta T will be very low, or none. The above table shows the maximum delta T preferred for fixed bed operation.

THE ROLE OF HYDROGEN

Although it is not essential to have hydrogen present during processing, the presence of hydrogen is beneficial in extending catalyst life and increasing distillate yields and conversion of reactants.

The role of hydrogen in the upgrading process is not completely understood. It is probably not reacting with oxygen compounds in the feed, as taught in U.S. Pat. No. 4,544,792, which is incorporated by reference. It is believed that the hydrogen does not act with any metal on the catalyst to hydrogenate olefins or dienes. The process works well when the catalyst has no hydrogenation/dehydrogenation components, e.g., when the zeolite is in the H-form.

The shape selective zeolites are believed, at the reaction conditions used herein, to create small amounts of atomic hydrogen which is extremely reactive and which reacts with the diene components of the feed, or reactive intermediates formed by the dienes and to a lesser extent with olefins in the feed.

The hydrogen may also react with nitrogen impurities which are in the feed, and release ammonia, and this may in some way alter the selectivity of the catalyst. The hydrogen probably also hydrogenates, to some extent, coke precursors.

Some benefits will be seen when the feed contains as little as 1 to 5 mole % H2. Operation with 5 to 50 mole % H2 in the reaction zone is preferred, with 10 to 30 mole % H2 being especially preferred. Operation with 0.1:1 to 1:1 H2:hydrocarbon ratios (molar basis) gives good results.

FEED PRETREATMENT

The feed should be pretreated to reduce the basic nitrogen content to less than 1 ppm, preferably to less than 0.5 wt. ppm, and ideally to less than 0.1 wt. ppm basic nitrogen, and most preferably to 0.05 wt. ppm basic nitrogen, or less.

Many refinery LPG streams will, using conventional methods of analysis, such as UOP method 430-70T, may seem to have relatively low levels of nitrogen, on the order of 0.1-0.2 ppm, while actually having about 1 ppm nitrogen. This test method involves flashing the vapor, passing the vapor through an acid wash, and analyzing the acid spectrophotometrically for nitrogen. We determined that this was not a reliable test method for finding 0.05 to 0.1 ppm nitrogen in a refinery LPG stream in a refinery laboratory.

A simple, and accurate analytical procedure was developed, using multiple stages of water extraction to remove the nitrogen compounds from the LPG, and then analyze the water extract from each stage for nitrogen. Using this method the refinery LPG stream referred to above consistently had about 1 ppm nitrogen, whereas the flash vaporization method gave results of 0.1 to 0.2 ppm nitrogen.

Although continuous water extraction of LPG is fairly easy to do continuously, on a large scale, it was harder to do in the laboratory. A simple batch method was developed as a laboratory test, adding roughly equal weights of water and LPG to an LPG cylinder, rolling it on a drum roller of 0.5-1 hour, and then allowing it to stand for about ½ hour for phase separation. The water phase was then drained out of the cylinder through the gas valve, using a high pressure flexible hose. Both the water extract, and the LPG (via another water extraction on a small sample) were then analyzed for nitrogen.

Water washing, preferably with a slightly acidified water stream, can reduce the combined nitrogen content of the feed to the desired level.

Other acidic substances may be used to pretreat the feed. Such acidic materials include ion exchange resins in the acid form, activated alumina, fresh or spent FCC catalyst, shape selective zeolites, and the like.

Process conditions for feed pretreatment, when using a solid bed, include the following:

|  | Acceptable | Preferred | Most Preferred |
|---|---|---|---|
| Temperature | 50–250 F. | 60–150 F. | 70–100 F. |
| Pressure |  | liquid phase preferred |  |
| LHSV | 0.01–100 | 0.1–50 | 0.5–20 |
| Maximum ppm N in Effluent | 1 | 0.1 | 0.05 |

The process works especially well when a combination of pretreatment processes is used, i.e., when there are at least two stages of feed pretreatment to remove nitrogen.

Liquid/liquid extraction of basic nitrogen compounds is a preferred pretreatment method. Any liquid which has an affinity for basic nitrogen compounds, and which is immiscible with the hydrocarbon feed, can be used. Suitable liquid extractants can be selected from water, and other liquids such as Sulfolane, glycols, alcohols, and mixtures thereof.

Liquid/liquid extraction is highly preferred over use of acidic solids. Ion exchange resins work to take basic nitrogen out of the feed but only one time. For reasons which are not completely understood, the resins can not be regenerated.

Water washing, preferably with acidified water, is an especially preferred way to remove the bulk of the basic nitrogen compounds present. A simple, multi-stage water washing feed pretreatment works, and can be run continuously. The only drawback to water washing is that its efficiency declines when the amine concentration in the hydrocarbon stream to be treated is unusually low, or unusually high.

The distribution coefficient for DEA between H2O and LPG was determined experimentally by contacting DEA spiked water with pure Matheson LPG and multiple contacts of a refinery LPG stream with pure water.

Figure 1:
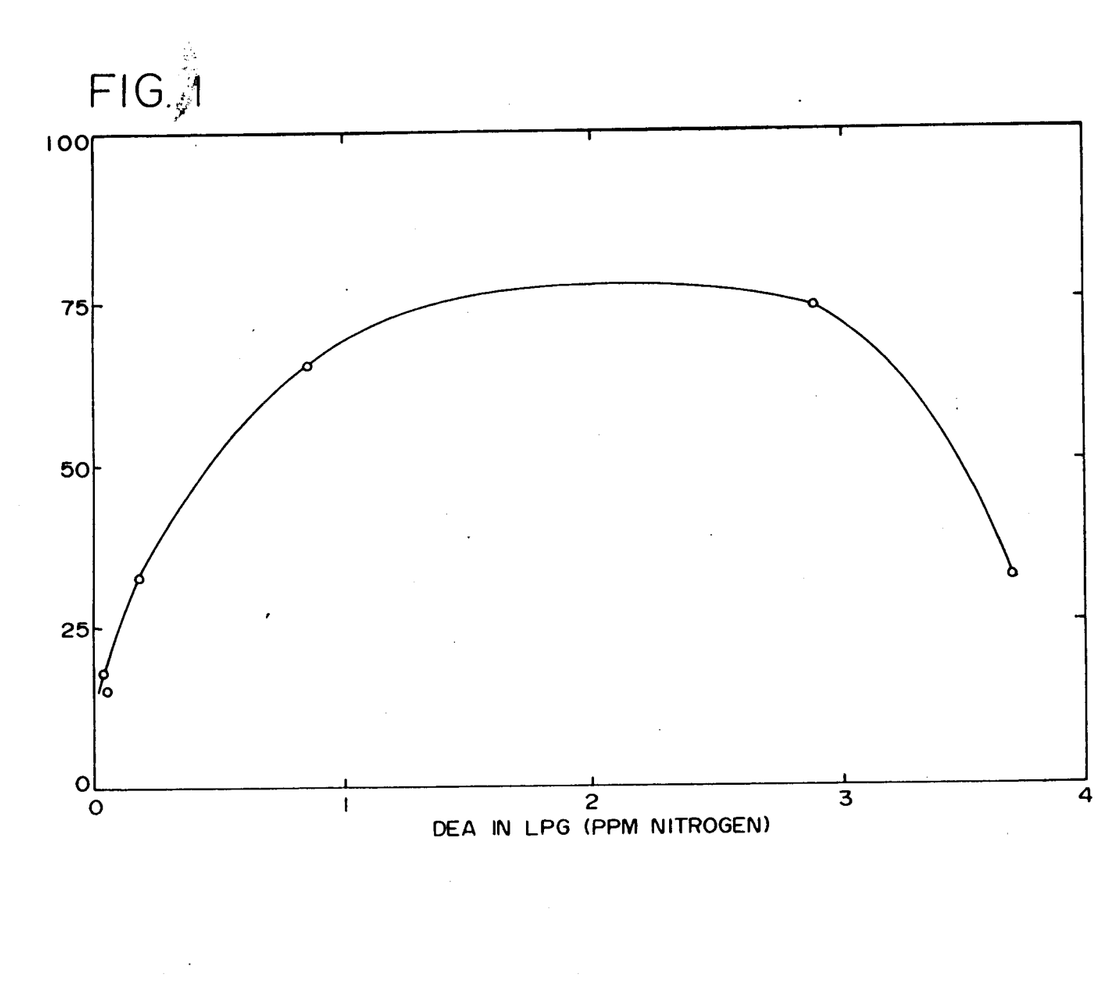
FIG. 1 shows the distribution of DEA between water and LPG.

As shown in FIG. 1, the distribution coefficient increased from about 15 for 0.05 ppm N in LPG to about 65 for 1 ppm N. At high levels of N, around 130 ppm in LPG, the distribution coefficient decreased to about 3. In the range of 2–5 ppm N, the water nitrogen levels are outside the limits of our analytical tests so no quantitative results could be obtained, however qualitatively the distribution coefficient in this region is above 20.

Because it was difficult to accurately measure these low nitrogen levels in hydrocarbon, the N levels were calculated from the difference in the water N levels, so there is some uncertainty about the distribution coefficient at the 0.2 and 0.9 ppm N in LPG level.

To be conservative, we would use a distribution coefficient no larger than 15, or even lower, around 10 or 11 to provide a conservative design. Using a value of 11.5 for a distribution coefficient, 240 lb/min (28 gpm) of water is required to reduce 750 lb/min of LPG from 3 ppm N to 0.05 ppm N in a 3 stage countercurrent extraction column.

Where costs of liquid/liquid extraction to remove basic N must be minimized, or to achieve an added measure of security, one or more stages of solid extraction may, in some circumstances, be substituted for, or used in conjunction with, the liquid/liquid extraction step.

Figure 2:
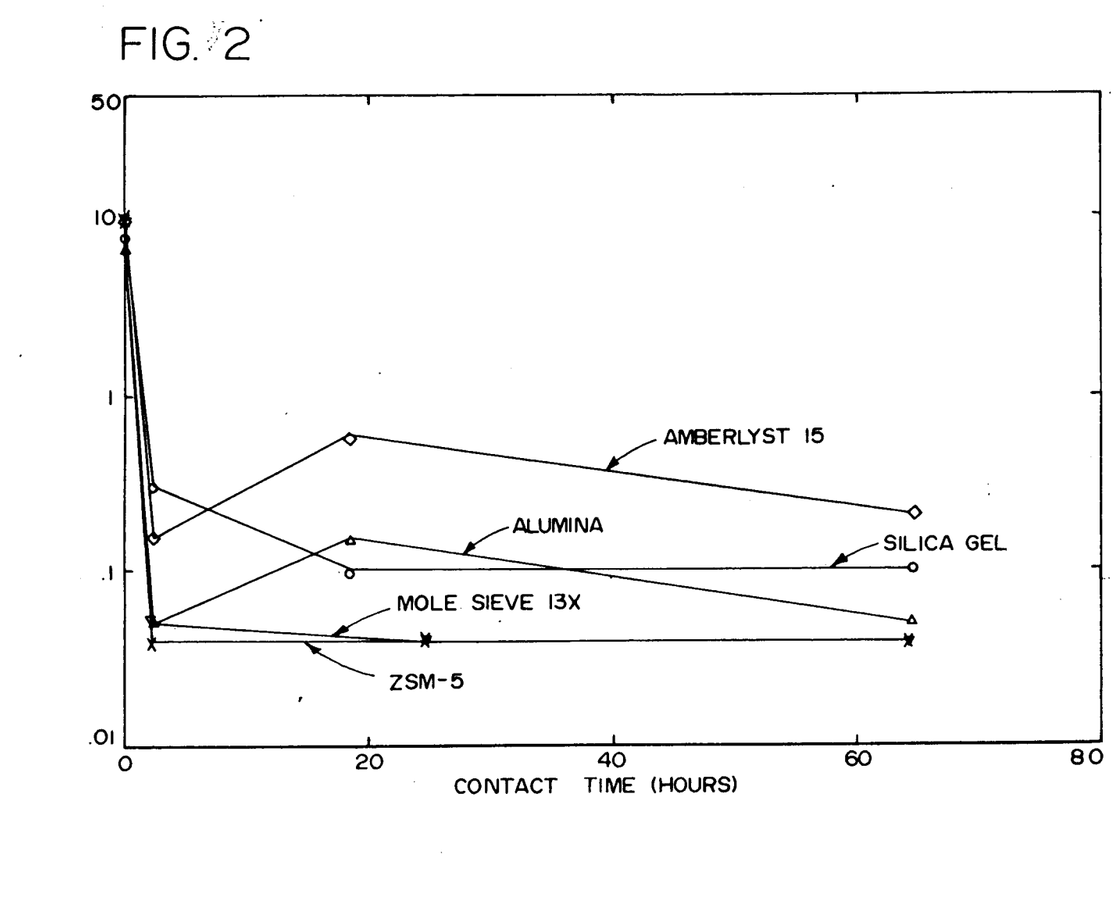
FIG. 2 shows the effectiveness of several sorbents for removal of DEA from hexene.

FIG. 2 shows the relative efficiency of various sorbents for removal of basic N from hexene/DEA mixtures. Hexene was used, rather than LPG because hexene is much easier to work with in the laboratory, and the results are believed comparable. Although this Figure shows that various solid sorbents can be used for hexene/DEA mixtures, later work showed that this was not always transferable to LPG/N mixtures.

When sorbent beds are used downstream of, or instead of, a liquid/liquid extraction zone, the beds are preferably sized to provide a liquid hourly space velocity of 0.1 to 10 hr$^{-1}$, and most preferably a liquid hourly space velocity of 0.2 to 5 hr$^{-1}$.

Sorbent bed size must be increased about 2-3 fold when no water washing is used upstream.

Sorbent beds in parallel may be used to permit on stream regeneration of an absorbent bed. Beds of ion-exchange resin may be regenerated by conventional means, e.g., by circulating an acid solution over the bed. If polymers or tar if formed on the resin bed by some catalytic action, the resin will have to be replaced, rather than regenerated.

Zeolitic materials, and other solids which can tolerate high temperatures, may be regenerated by heating to a high enough temperature to desorb the adsorbed basic nitrogen compounds. Alumina may be regenerated by air oxidation to oxidize or drive off the basic nitrogen containing compounds. Oxidative regeneration can be used to remove polymer or tar that forms on the sorbent bed via catalytic reactions.

DIENE CONTROL

When naphtha boiling range feeds are used, they may contain large amounts of dienes (rendering them unsuitable for conventional hydroprocessing) and large amounts of sulfur. The process of the present invention tolerates these poisons fairly well. When large diene contents are present, in excess of 0.5 wt %, then reaction temperatures in the olefin upgrading step should, for the initial stages at least, be kept relatively low to minimize gum formation in the preheater.

HYDROGEN CO-FEED AND NITROGEN REMOVAL

The process of the present invention works especially well when both hydrogen co-feed and feed pretreatment, to remove basic nitrogen compounds, are practiced together. The combination permits unusually long run lengths to be achieved, or very high space velocity to be maintained.

Although the reason for the unexpected increase in catalyst stability is not known, it is speculated that each step removes most efficiently the poisons lefts behind by the other step. The poisons not efficiently removed by water washing are the poisons most readily removed by the presence of hydrogen in the oligomerization reactor. The two steps are complementary, and make the process far more tolerant of upsets that are an everyday occurrence in modern refineries.

EXPERIMENTS

Several experiments were conducted to test the effectiveness of various feed pretreatments and of hydrogen co-feed.

The tests used the same feed, a specified feed pretreatment (ranging from none to water washing to adsorbent bed contact) and the same oligomerization treatment.

FEEDSTOCK

A feedstock analysis is presented below.

| | |
|---|---|
| C3 = | 30.7 wt % |
| C3 | 10.7 wt % |
| 1,3 C4 = = | 0.4 wt % |
| T2 C4 = | 9.0 wt % |
| C2 C4 = | 6.1 wt % |
| iC4 = | 14.4 wt % |
| 1 C4 = | 8.8 wt % |
| iC4 | 15.3 wt % |
| nC4 | 4.6 wt % |
| | 100.0 |

Basic Nitrogen 1.01 wt ppm

FEED PRETREATMENT

All feed pretreatment occurred in the liquid phase, at 250 psig.

When a solid bed feed pretreater was used, the bed contained 275g of Amberlyst-15 resin. The feed rate was 70 cc/hr, downflow through the bed, for a weight hourly space velocity of 0.15. The material exiting the resin bed was estimated to contain slightly less than 0.1 wt ppm basic N.

When water washing was used for feed pretreatment, the feed was passed through three stages of contact with equal volumes of water at room temperature. Based on other work, the basic nitrogen content of the water washed feed was estimated to be below 0.1 wt ppm.

A longer term test was conducted using Amberlyst 15 ion exchange resin to pretreat an LPG feed. This resin was chosen because of its ready availability commercially, and because it had previously been used successfully to remove nitrogen compounds from jet fuel, as reported Prudlich, M. E. et. al.,"Shale Oil Denitrogenation with Ion Exchange" parts 1, 2, and 3 as reported in Ind. Eng. Chem. Process Des. Dev. 1986, 25, 742-762.

A 1000 cc hoke vessel was filled with 275 g of fresh dry resin in the H+state. The resin was preswelled with hexene and used on line to treat a refinery LPG stream at a 0.15/hour space velocity. Calculations indicated that this amount of Amberlyst 15 should have lasted more than 50 years, based on 1 ppm N in the feed, assuming the acid sites on the resin were used stoichiometrically. While the unit worked efficiently at first to remove nitrogen, and did improve the operation of a downstream olefin oligomerization unit, there was an apparent nitrogen breakthrough after only 14 days on stream. The breakthrough was confirmed by the measured reduction in acid sites on the resin from 3.5-3.8 meq/gm to 1.8 meq/gm, uniformly through the resin bed. Attempts at regenerating the resin by ion exchange with acid resulted in an increase in acid sites to 2.5 meq/gm, indicating that the resin acid sites had become permanently blocked.

An analysis of spent and fresh resins was conducted to try to determine what had caused the permanent deactivation. The spent resin contained a higher percentage of C-H containing species than the fresh resin. It is believed that the deactivation of the Amberlyst resin resulted from polymerization of one of the feed components which resulted in pore plugging.

Because of the catalytic activity of some sorbents, such as the ion exchange resins, and the reactivity of the feeds contemplated for use herein, it usually will be preferred to operate with water extraction rather than a solid sorbent bed. If a sorbent bed is to be used, it should first be tested in the laboratory to determine that it is efficient at absorbing nitrogen compounds, and free of undesirable catalytic properties.

OLEFIN OLIGOMERIZATION

All tests were run at 800 psig in the oligomerization reaction zone. The oligomerization reactor was a fixed bed reactor, having an internal diameter of 1.25 cm and containing 60 cc of catalyst in each of 3 beds in series. When hydrogen was added to the feed, it was added at a rate of 250 SCFB.

The olefin oligomerization catalyst was a 65/35 mix of H-ZSM-5 in alumina. The ZSM-5 had a silica to alumina mole ratio of about 70/1, an alpha activity (pure zeolite basis) of about 230–240.

Each test lasted about three weeks. Reaction conditions included a temperature of 480–580° F., a 1.0 WHSV on olefin, and 800 psig pressure.

The total liquid product from the oligomerization reactor was analyzed for basic nitrogen. This is an indication whether or not the catalyst has been poisoned with basic nitrogen compounds. Because the catalyst acid sites will react with, or complex, basic N, the presence of basic N in the liquid product is an indication that the catalyst bed is saturated with, or poisoned by, basic N entering with the feed.

Figure 3:
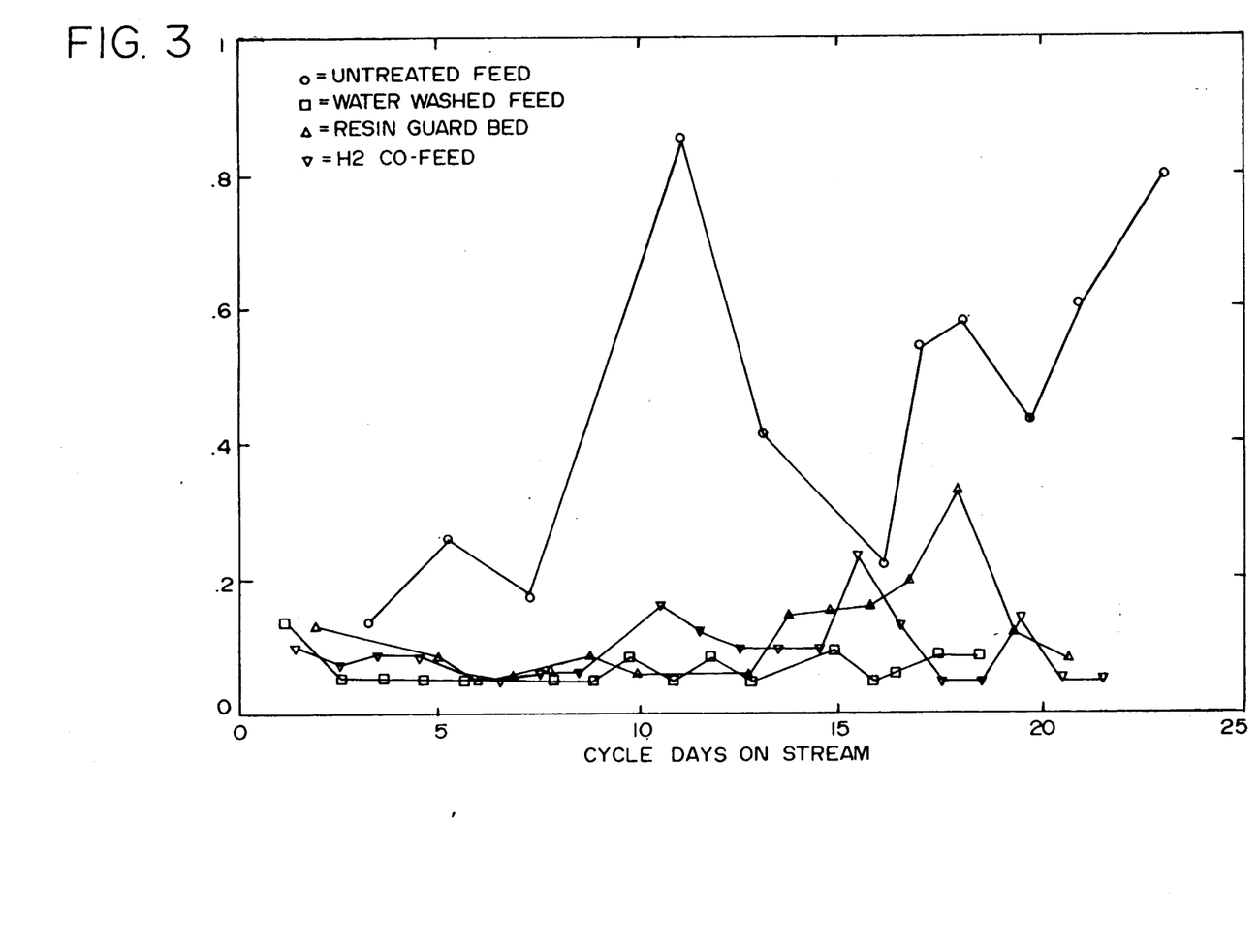
FIG. 3 shows basic nitrogen in oligomerized liquid product as a function of feed pretreatment and H2 addition.

The experimental results are presented graphically in FIG. 3, where:
 o=Untreated Feed (1.0 ppm N)
 =Water Washed Feed (Less Than 0.1 ppm N)
 =Resin Guard Bed (about 0.1 ppm N)
 =H2 co-feed (the feed contained 1.0 ppm N)

Untreated feed rapidly kills the catalyst. The data in FIG. 3 show that there is rapid contamination of the bed of oligomerization catalyst when untreated feed is used. This means that the oligomerization reactor performance will decline rapidly, and/or that the oligomerization reactor must be frequently regenerated.

Water washing of feed is effective at preventing nitrogen contamination of the oligomerization catalyst.

Resin guard bed treating is effective for a time, but in the example there was eventually breakthrough of basic nitrogen into the product, indicating some poisoning of the oligomerization catalyst.

Hydrogen co-feed was very effective at eliminating basic nitrogen compounds from the oligomerization zone liquid product.

PROCESS OPTIMIZATION

Preferably, feed pretreatment to reduce the total nitrogen content is coupled with hydrogen addition to the oligomerization reactor to achieve best results. To some extent, better feed preparation will compensate for lower hydrogen partial pressure, and vice versa. Ideally, essentially all of the basic nitrogen in the feed is removed by the feed pretreatment so that less than 0.05 ppm basic nitrogen remains in the feed to the oligomerization reactor. Preferably hydrogen is present, in a roughly 0.1:1 to 0.5:1 molar ratio with hydrocarbon feed.

Use of a two stage feed pretreatment process, with an aqueous primary stage and a zeolitic secondary stage, will provide enhanced operational stability.

Although fixed bed operation of the oligomerization reactor is preferred, because of simplicity and low cost, it is also possible to operate with a fluidized bed or with a moving bed design, which permits continuous removal and replacement of spent catalyst. Swing reactors are another way to tolerate a higher catalyst aging rate while remaining on stream all the time.

SORBENT REGENERATION

The adsorbent beds may be regenerated using conventional techniques, e.g., acid wash for ion exchange resin, and high temperature stripping or burning for alumina, zeolite, etc.

OLIGOMERIZATION CATALYST REGENERATION

Although the practice of the present invention greatly extends catalyst cycle lengths, there will be a gradual accumulation of coke and gum material which will cause deactivation of the oligomerization catalyst.

Hot hydrogen stripping will, in many instances, restore some catalyst activity. Conventional hydrogen stripping conditions may be used.

For complete regeneration of the catalyst, contact with an oxygen containing gas, preferably air added to a circulating nitrogen stream, can be used to burn off coke and gummy hydrocarbon deposits. Conventional catalyst regeneration conditions can be used.

The process of the present invention provides refiners with an efficient way of upgrading light, relatively low value, olefinic streams to more valuable gasoline and distillate products. The process is especially efficient at converting C2 to C5 olefins into more valuable products, despite the presence of relatively large amounts of basic nitrogen in such refinery streams. The process is very tolerant of light olefins such as ethylene and can easily accommodate heavy olefins boiling in the naphtha range.

With reduced limits on gasoline RVP refiners now have a way to increase gasoline yields without adding more light ends to the gasoline pool. Light olefin streams can be upgraded into more valuable, heavier liquid products without resort to HF or sulfuric acid alkylation.

We claim:

1. A process for upgrading an olefinic feed comprising C2 to C10 olefins containing basic nitrogen compounds which has been produced by thermal or catalytic cracking of a heavier liquid hydrocarbon by contacting the olefinic feed with an upgrading catalyst comprising a zeolite having a Constraint Index of about 1 to 12, a silica to alumina mole ratio of at least 12 at olefin oligomerization reaction conditions including a superatmospheric pressure and in the presence of added hydrogen of about 0.01:1 to 1:1 to oligomerize at least a portion of the olefins in the feed to gasoline and distillate boiling range products, and wherein the hydrogen is present in an amount sufficient to extend the catalyst life of the upgrading catalyst relative to operation at superatmospheric pressure without any hydrogen added.

2. The process of claim 1 wherein the olefinic feed contains more than 1 wt. ppm of basic nitrogen compounds, and the basic nitrogen content of the feed is reduced by a feed pretreatment step prior to upgrading to reduce the basic nitrogen content of the feed below 0.1 wt ppm basic nitrogen.

3. The process of claim 2 wherein the basic nitrogen content of the feed is reduced below 0.05 wt ppm by pretreatment.

4. The process of claim 2 wherein the feed pretreatment to remove basic nitrogen compounds is selected from the group of water washing and contact with a solid, adsorbent having an affinity for basic nitrogen compounds.

5. The process of claim 4 wherein the feed pretreatment comprises at least two stages of contact, a first nitrogen removal stage comprising at least one of a water washing step or contact of feed with a solid bed of a an amorphous material having an affinity for basic nitrogen and a second nitrogen removal stage comprising contact with a bed of a zeolitic material selected from the group of large pore zeolites and zeolites with a Constraint Index of about 1 to 12.

6. The process of claim 1 wherein the hydrogen to hydrocarbon ratio in the oligomerization reaction zone is 0.05 to 0.5.

7. The process of claim 1 wherein the oligomerization reaction conditions include a pressure of 100 to 1000 psig, a temperature of 250° to 750° F., and wherein the hydrogen:hydrocarbon mole ratio is 0.2:1 to 1:1.

8. The process of claim 1 wherein the olefinic feed is an olefinic naphtha from catalytic cracking.

9. The process of claim 1 wherein the olefinic feed is a refinery produced liquified petroleum gas stream consisting essentially of hydrocarbons having from 2 to 5 carbon atoms.

10. A process for oligomerizing a light, normally gaseous olefinic feed, containing more than 0.5 wt ppm basic nitrogen compounds and comprising olefinic hydrocarbons having three to four carbon atoms produced by catalytic cracking of heavy, sulfur containing hydrocarbons boiling in the gas oil and heavier range to lighter products and H$_2$S, which lighter products are treated with an amine to remove H$_2$S and produce an amine treated, light, normally gaseous hydrocarbon stream containing a reduced H$_2$S content and more than 0.5 wt ppm basic nitrogen as a result of the amine treatment of the lighter products, to gasoline and distillate boiling range products comprising:

reducing the basic nitrogen content of the amine treated, light, normally gaseous olefinic feed by contacting said feed with a sorbent having an affinity for basic nitrogen compounds to reduce the basic nitrogen content of the olefinic feed below 0.1 wt ppm; and oligomerizing said olefinic feed with a basic nitrogen content below 0.1 wt ppm in an oligomerization reaction zone over an oligomerization catalyst, comprising a zeolite having a Constraint Index of about 1 to 12 and a silica to alumina mole ratio of at least 12, at olefin oligomerization conditions to produce gasoline and distillate boiling range products and wherein the olefin oligomerization reaction is conducted in the presence of added hydrogen, at a mole ratio of hydrogen to hydrocarbon of about 0.01:1 to about 1:1, and wherein the hydrogen is present in an amount sufficient to extend the catalyst life of the upgrading catalyst relative to operation at superatmospheric pressure without any hydrogen added.

11. The process of claim 10 wherein the oligomerization catalyst comprises ZSM-5 and the basic nitrogen content of said light normally gaseous hydrocarbon feed is reduced below 0.05 wt ppm.

12. The process of claim 10 wherein the basic nitrogen content of the feed is reduced by liquid liquid extraction with water.

13. The process of claim 10 wherein the olefin oligomerization reaction conditions include a temperature of about 250–700° F., a hydrocarbon feed weight hourly space velocity of about 0.1 to 10, and a catalyst zeolite alpha activity above about 100.

14. The process of claim 10 wherein the olefin oligomerization reaction is conducted at a temperature of about 300–550° F., a hydrocarbon weight hourly space velocity of 0.5 to 5, and a zeolite alpha activity above 150.

15. A process for producing gasoline and distillate boiling range products from a heavy hydrocarbon feed boiling in the gas oil and heavier range comprising:

(a) catalytically cracking said heavy feed at catalytic cracking conditions in a catalytic cracking unit to produce cracked products including olefinic C3 and C4 hydrocarbons and H2S;

(b) treating the olefinic C3 and C4 hydrocarbons with an amine to reduce the H2S content thereof and produce treated olefinic C3 and C4 hydrocarbon fraction containing more than 0.1 wt ppm basic nitrogen compounds as a result of the amine treating step;

(c) reducing the basic nitrogen content of the treated olefinic feed below 0.05 wt ppm basic nitrogen by extracting the basic nitrogen compounds from the treated feed with water to produce a water extracted olefinic feed with a reduced basic nitrogen content; and (d) oligomerizing the water extracted olefinic feed by contact with an upgrading catalyst comprising ZSM-5 having a silica to alumina mole ratio of at least 12, and an alpha value, on a pure ZSM-5 basis, of at least 100, at olefin oligomerization conditions including a superatmospheric pressure, a temperature of 250–750° F., the presence of added hydrogen, at a hydrogen to hydrocarbon hydrocarbon mole ratio of about 0.01:1 to about 0.5:1, and wherein hydrogen is present in an amount sufficient to extend the catalyst life of the upgrading catalyst relative to operation at superatmospheric pressure without any hydrogen added, and a hydrocarbon weight hourly space velocity of about 0.1 to 10 to oligomerize at least a portion of the olefins in the feed to a gasoline and distillate boiling range product.

* * * * *